(12) United States Patent
Crawford

(10) Patent No.: US 9,260,419 B2
(45) Date of Patent: Feb. 16, 2016

(54) POLYMORPHIC SALT OF A METAP-2 INHIBITOR AND METHODS OF MAKING AND USING SAME

(71) Applicant: Zafgen, Inc., Cambridge, MA (US)

(72) Inventor: Thomas Crawford, Essex, CT (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/399,387

(22) PCT Filed: May 7, 2013

(86) PCT No.: PCT/US2013/039877
§ 371 (c)(1),
(2) Date: Nov. 6, 2014

(87) PCT Pub. No.: WO2013/169727
PCT Pub. Date: Nov. 14, 2013

(65) Prior Publication Data
US 2015/0111964 A1    Apr. 23, 2015

Related U.S. Application Data

(60) Provisional application No. 61/643,586, filed on May 7, 2012.

(51) Int. Cl.
*C07D 407/08* (2006.01)
*C07D 303/36* (2006.01)

(52) U.S. Cl.
CPC ............ *C07D 407/08* (2013.01); *C07D 303/36* (2013.01)

(58) Field of Classification Search
CPC .................................................... C07D 407/08
USPC .................................. 514/475; 549/332, 551
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Tarnus et al. |
| 7,084,108 B2 | 8/2006 | Olson et al. |
| 7,268,111 B2 | 9/2007 | Olson et al. |
| 7,718,695 B2 | 5/2010 | Kim et al. |
| 8,349,891 B2 | 1/2013 | Crawford et al. |
| 8,735,447 B2 | 5/2014 | Crawford et al. |
| 2004/0067266 A1 | 4/2004 | Toppo |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2012/0034233 A1 | 2/2012 | Hughes et al. |
| 2013/0035483 A1* | 2/2013 | Zeng et al. ................... 540/456 |

FOREIGN PATENT DOCUMENTS

| | | |
|---|---|---|
| EP | 0682020 A1 | 11/1995 |
| WO | WO-99/59986 A1 | 11/1999 |
| WO | WO-99/59987 A1 | 11/1999 |
| WO | WO-2000/064876 A1 | 11/2000 |
| WO | WO-03/027104 A1 | 4/2003 |
| WO | WO-2004/033419 A1 | 4/2004 |
| WO | WO-2005/082349 A1 | 9/2005 |
| WO | WO-2006/080591 A1 | 8/2006 |
| WO | WO-2010/065877 A2 | 6/2010 |
| WO | WO-2010/065879 A2 | 6/2010 |

(Continued)

OTHER PUBLICATIONS

U.S. Appl. No. 14/178,788, Crystalline Solids of a METAP-2 Inhibitor and Methods of Making and Using Same, filed Feb. 12, 2014.
Anderson, Hamilton H., "The Use of Fumagillin in Amoebiasis," *Annals New York Academy of Sciences*, 1118-1124. (1952).
Benny, Ofra, et al., (2008) "An Orally Delivered Small-Molecule Formulation with Antiangiogenic and Anticancer Activity," Nature Biotechnology, 26, 7:799-807.
Bernier et al. (2005) "Fumagillin class inhibitors of methionine aminopeptidase-2," *Drugs of the Future* 30(5): 497-500.
Brakenhielm, E., et al., (2004) "Angiogenesis Inhibitor, TNP-470, Prevents Diet-Induced and Genetic Obesity in Mice," Circulation Research, http://circres.ahajournals.org (accessed on Feb. 8, 2007).
Braunwald, et al.. "Obesity" in Harrison's Principles of Internal Medicine, 15th Ed., 479-86 (2001).
DiPaolo, J.A., et al. (1958-1959) "Studies on the Carcinolytic Activity of Fumagillin and Some of its Derivatives," *Antibiotics Annual*, 541-546.
Drevs, Joachim, et al. (2003) "Antiangiogenic Potency of FK866/K22.175, a New Inhibitor of Intracellular NAD Biosynthesis, In Murine Renal Cell Carcinoma," Anticancer Research 23: 4853-4858.
Dumas, J., et al., "Synthesis and Structure Activity Relationships of Novel Small Molecule Cathepsin D Inhibitors," Bioorganic & Medicinal Chemistry Letters 9 (1999) 2531-2536.

(Continued)

*Primary Examiner* — Taofiq A Solola
(74) *Attorney, Agent, or Firm* — Goodwin Procter LLP

(57) ABSTRACT

The disclosure is in part directed to crystalline forms of an oxalate salt of 6-O-(4-dimethylaminoethoxy)cinnamoyl fumagillol.

11 Claims, 15 Drawing Sheets

(56) References Cited

FOREIGN PATENT DOCUMENTS

| WO | WO-2010/065881 A2 | 6/2010 |
|----|-------------------|--------|
| WO | WO-2010065883 A2 | 6/2010 |
| WO | WO-2011/044506 A2 | 4/2011 |
| WO | WO-2011/088055 A2 | 7/2011 |

OTHER PUBLICATIONS

Eder, JP, et al., (2006) "Phase 1 Dose Escalation Safety & Tolerance Study of PPI-2458 in Subjects with Non-Hodgkin's Lymphoma or Solid Tumors," (Presented on Nov. 7-10, 2006 at EORTC-NCI-AACR Symposium on "Molecular Targets and Cancer Therapeutics.").

European Search Report for EP 09798793 dated Oct. 11, 2011, 9 pages.

Everhart (1993) "Contributions of Obesity and Weight Loss to Gallstone Disease," *Ann Intern Med.* 119:1029-1035.

Hughes et al. "Ascending dose-controlled trial of beloranib, a novel obesity treatment for safety, tolerability, and weight loss in obese women" *Obesity (Silver Spring).* Sep. 21, 2013(9):1782-8. doi:10.1002/oby.20356. Epub May 25, 2013.

Ingber et al. (1990) "Synthetic analogues of fumagillin that inhibit angiogenesis and suppress tumour growth," *Nature* 348: 555-557.

International Search Report and Written Opinion for International Application No. PCT/US2013/039877 dated Nov. 11, 2014 (8 pages).

International Search Report for International Application No. PCT/US2013/039877 dated Jul. 31, 2013 (4 pages).

International Search Report for International Application PCT/US2010/052050.dated Mar. 25, 2011 (3 pages).

Jeong, et al., "Total Synthesis and Antiangiogenic Activity of Cyclopentane Analogues of Fumagillol," Bioorg. Med. Chem. Lett. 15 3580-83 (2005).

Kim et al., "General Pharmacology of CKD-732, a New Anticancer Agent: Effects on Central Nervous, Cardiovascular, and Respiratory System," Biol. Pharm. Bull., vol. 28, pp. 217-223 (2005).

Kim, YM, et al. (2007) "Assessment of the Anti-Obesity Effects of the TNP-470 Analog, CD-732," Journal of Molecular Endocrinology 38, 455-465.

Kruger, Erwin, A., (2000) "TNP-470: An Angiogenesis Inhibitor in Clinical Development for Cancer," Exp. Opin. Invest. Drugs 9(6), pp. 1383-1396.

Molina et al. (1997) "Potential Efficacy of Fumagillin in Intestinal Microsporidiosis Due to Enterocytozoon Bieneusi in Patients with HIV Infection: Results of a Drug Screening Study," *AIDS*, 11:1603-1610.

Molina et al. (2002) "Fumagillin Treatment of Intestinal Microsporidiosis," *N. Engl. J. Med.* 346(25): 1963-1969.

Molina, et al.(2000) "Trial of Oral Fumagillin for the Treatment of Intestinal Microsporidiosis in Patients with HIV Infection," *AIDS*, 14:1341-1348.

Naganuma, Yasuko, et al. (2011) "Metronomic Doxifluridine Chemotherapy Combined with the Anti-Angiogenic Agent TNP=470 Inhibits the Growth of Human Uterine Carcinosarcoma Xenografts," Cancer Sci 102(8): pp. 1545-1552.

National Task Force on the Prevention and Treatment of Obesity (1993) "Very Low-Calorie Diets," *JAMA* 270(8):967-974.

Noel et al. (2009) "Increased Risk of Acute Pancreatitis and Biliary Disease Observed in Patients with Type 2 Diabetes," *Diabetes Care* 32(5):834-838.

Pagliarulo et al. (2004) "Gallstone disease and related risk factors in a large cohort of diabetic patients," *Digestive and Liver Disease* 36:130-134.

Picoul et al. (2003) "Progress in fumagillin synthesis," *Pure Appl. Chem.* 75(2-3): 235-249.

Rupnick, MA (2002) "Adipose Tissue Mass Can be Regulated Through the Vasculature," PNAS 99, 10730-10735.

Seneca et al. (1956) "Amebiasis: a review. II. Laboratory diagnosis, differential diagnosis and therapy," *Am J. Digestive Dis.* 1: 310-322.

Shin, Sj (2010) "A Phase I Pharmacokinetic and Pharmacodynamic Stdy of CKD-732, an Antiangiogenic Agent, in Patients with Refractory Solid Cancer," Invest New Drugs 28:650-658, (2010) Published online Jul. 8, 2009.

Weinsier et al. (1993) "Gallstone Formation and Weight Loss," *Obesity Research* 1(1):51-56.

Weinsier, et al. (1995) "Medically Safe Rate of Weight Loss for the Treatment of Obesity: A Guideline Based on Risk of Gallstone Formation," *The American Journal of Medicine* 98:115-117.

Winter et al. (2006) "Endothelial $\alpha_v\beta_3$ Integrin-Targeted Fumagillin Nanoparticles Inhibit Angiogenesis in Atherosclerosis," *Arterioscler Thromb Vasc Biol.*: 2103-2109.

Yanai, Shigeo, et al. (1995) "Antitumor Effect of Arterial Administration of a Medium-Chain Triglyceride Solution of an Angiogenesis Inhibitor, TNP-470, in Rabbits Bearing VX-2 Carcinoma," Pharmaceutical Research 12(5): pp. 653-657.

Yanai, Shigeo, et al., (1994) "Antitumor Activity of a Medium-Chain Triglyceride Solution of the Angiogenesis Inhibitor TNP-470 (AGM-1470) when Administered Via the Hepatic Artery to Rats Bearing Walker 256 Carcinosarcoma in the Liver," The Journal of Pharmacology and Experimental Therapeutics 271(3): pp. 1267-1273.

* cited by examiner

FT-IR SPECTRUM OF FORM A

¹H NMR SPECTRUM (WITHOUT D₂O SPIKE) OF FORM A $^1$H NMR SPECTRUM (WITH D$_2$O SPIKE) OF FORM A

AMORPHOUS MATERIAL

XRPD OF AMORPHOUS MATERIAL

XRPD OF FORM B

DSC/TGA TRACE OF FORM A

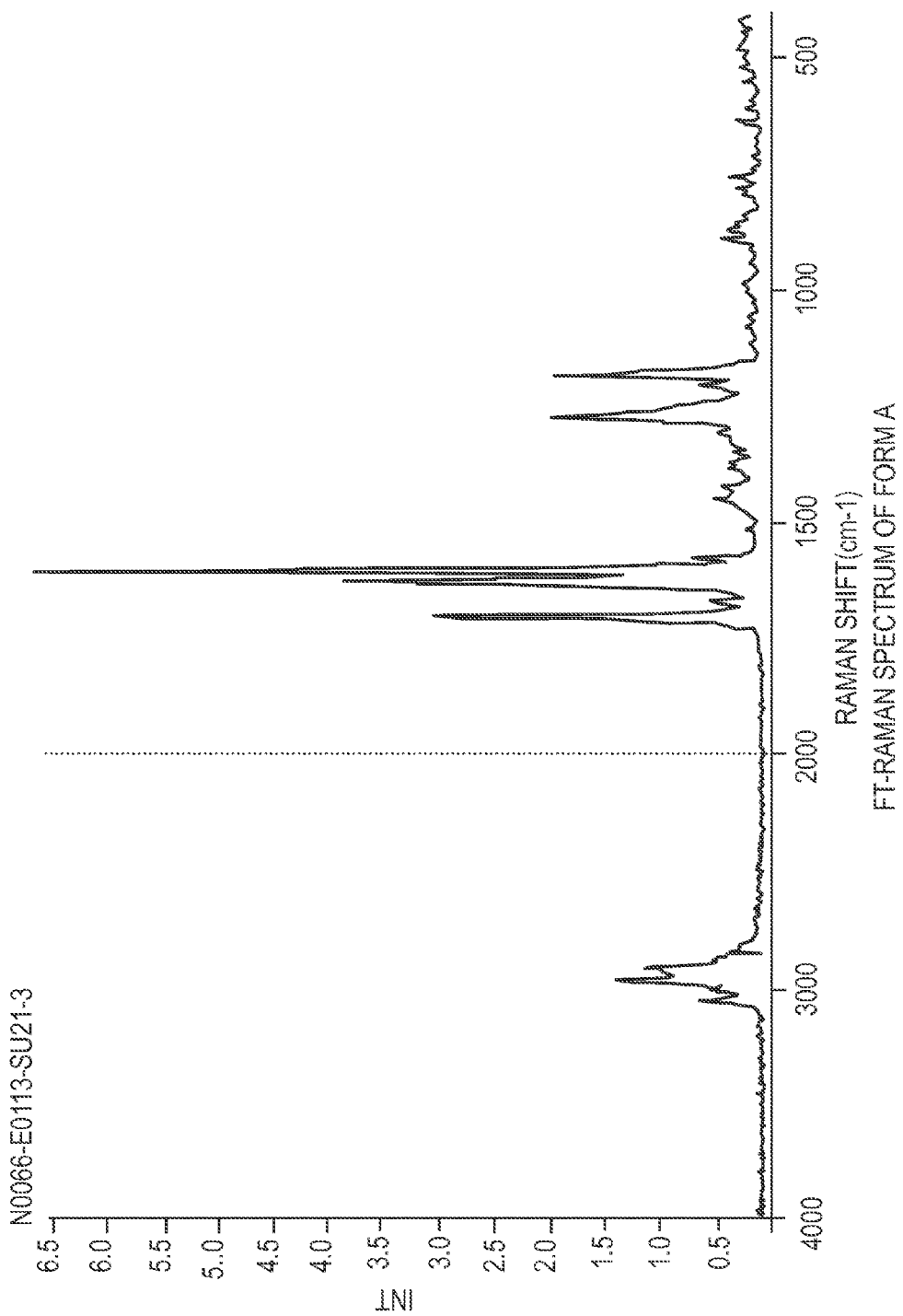

POLYMORPHIC SALT OF A METAP-2 INHIBITOR AND METHODS OF MAKING AND USING SAME

CROSS REFERENCE TO RELATED APPLICATIONS

This application claims priority to U.S. Provisional Ser. No. 61/643,586 filed May 7, 2012, hereby incorporated by reference in its entirety.

BACKGROUND

MetAP2 encodes a protein that functions at least in part by enzymatically removing the amino terminal methionine residue from certain newly translated proteins, such as, glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) *Cancer Res* 63:7861) and infectious diseases, such as, microsporidiosis, leishmaniasis, and malaria (Zhang et al. (2002) *J. Biomed Sci.* 9:34). Notably, inhibition of MetAP2 activity in obese and obese-diabetic animals leads to a reduction in body weight in part by increasing the oxidation of fat and in part by reducing the consumption of food (Rupnick et al. (2002) *Proc Natl Acad Sci USA* 99:10730).

6-O-(4-Dimethylaminoethoxy)cinnamoyl fumagillol is a METAP2 inhibitor and is useful in the treatment of, e.g., obesity. 6-O-(4-Dimethylaminoethoxy)cinnamoyl fumagillol is characterized by formula I:

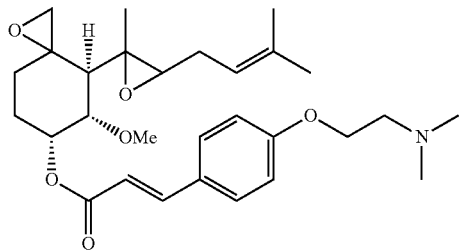 [SMILES: CO[C@@H]1[C@H](OC(=O)/C=C/c2ccc(OCCN(C)C)cc2)CCC2(CO2)[C@H]1C1(C)OC1CC=C(C)C]

An amorphous form of a hemioxalate salt of 6-O-(4-dimethylaminoethoxy)cinnamoyl fumagillol has been prepared. However, the existence or preparation of a crystalline form of the hemioxalate salt of 6-O-(4-Dimethylaminoethoxy)cinnamoyl fumagillol does not appear to be disclosed in the art.

Polymorphism is the ability of a substance to crystallize in more than one crystal lattice arrangement. Crystallization, or polymorphism, can influence many aspects of solid state properties of a drug substance. A crystalline substance may differ considerably from an amorphous form, and different crystal modifications of a substance may differ considerably from one another in many respects including solubility, dissolution rate and/or bioavailability. Generally, it is difficult to predict whether or not a given compound will form various crystalline solid state forms. It is even more difficult to predict the physical properties of these crystalline solid state forms. Further, it can be advantageous to have a crystalline form of a therapeutic agent for certain formulations, e.g., formulations suitable for subcutaneous use.

SUMMARY

In an embodiment, provided herein is a composition comprising a crystalline form of the hemioxalate salt of 6-O-(4-dimethylaminoethoxy)cinnamoyl fumagillol. A crystalline form of an hemioxalate salt of 6-O-(4-dimethylaminoethoxy) cinnamoyl fumagillol, and hydrates thereof is also provided herein, characterized by a powder X-ray diffraction pattern having a characteristic peak in degrees 2θ at about 7.1, or for example, characterized by a powder X-ray diffraction pattern having characteristic peaks in degrees 2θ at 4.7, 7.1, and 13.4, or for example, characterized by a powder X-ray diffraction pattern having characteristic peaks in degrees 2θ at 4.7, 7.1, 9.5, 12.9, 13.4, and 16.8, or for example, characterized by a powder X-ray diffraction pattern having characteristic peaks in degrees 2θ at 2.3, 4.7, 7.1, 9.5, 11.9, 12.9, 13.4, 14.3, 14.6, 15.6, 16.8, and 20.3, e.g., characterized by the crystallization pattern shown in FIG. 1 or FIG. 2. In some embodiments, the powder X-ray diffraction pattern may be obtained using Cu Kα radiation.

In one embodiment, the hemioxalate salt of 6-O-(4-dimethylaminoethoxy)cinnamoyl fumagillol may have a $^1$H NMR spectrum substantially in accordance with the pattern shown in FIG. 7A.

Also provided herein is a process for preparing a crystalline form of a hemioxalate salt of 6-O-(4-dimethylaminoethoxy) cinnamoyl fumagillol (e.g., form A), comprising:

a) preparing a solution of a hemioxalate salt of 6-O-(4-dimethylaminoethoxy)cinnamoyl fumagillol, e.g., the solution may comprise ethyl acetate and heptane;

b) heating the solution, e.g., to about 35 to about 55° C., e.g., to about 40° C., to substantially or completely dissolve the 6-O-(4-dimethylaminoethoxy)cinnamoyl fumagillol;

c) adjusting the temperature so that solid precipitates out of the solution; and d) isolating the crystalline form of the hemioxalate salt of 6-O-(4-dimethylaminoethoxy)cinnamoyl fumagillol. Such a process that includes adjusting temperature may comprise cooling the solution to about 5° C. or less, or to about 2° C. to about 10° C.

A pharmaceutical composition comprising the crystalline form provided herein and a pharmaceutically acceptable excipient is contemplated, for example, a composition that is a suspension formulation suitable for subcutaneous injection. Provided herein is a drug substance comprising at least a detectable amount of the provided crystalline form.

A method of treating obesity in a patient in need thereof is also provided that includes administering to the patient an effective amount of a crystalline form provided herein. Also provided herein is a method of treating obesity in patient in need thereof, comprising subcutaneously administering a composition comprising a disclosed crystalline form of 6-O-(4-dimethylaminoethoxy)cinnamoyl fumagillol hemioxalate salt.

BRIEF DESCRIPTION OF THE FIGURES

FIG. 13 depicts the FT-IR Raman of the crystal form prepared by Example 7 (Form A).

DETAILED DESCRIPTION

Figure 1:
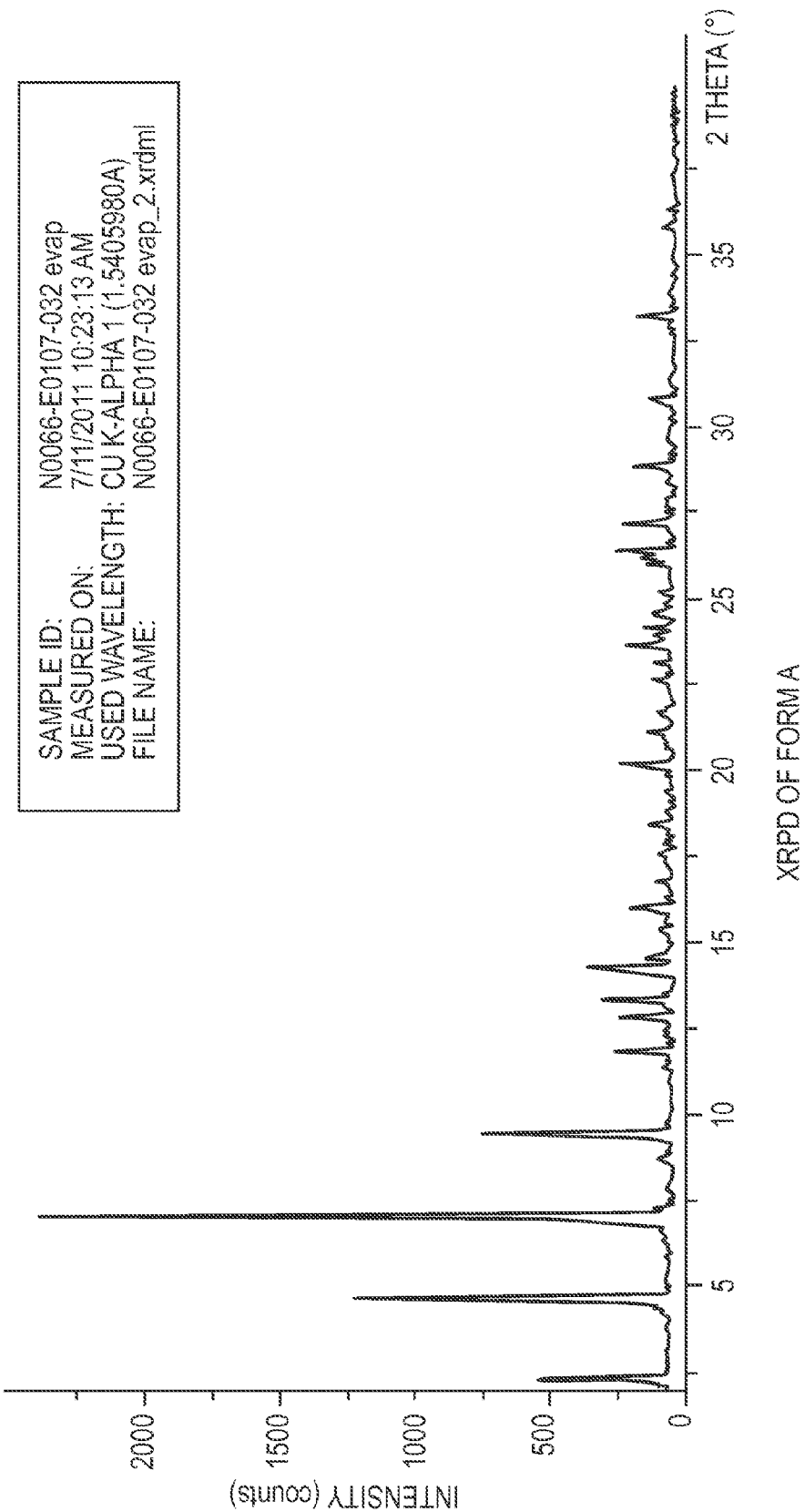
FIG. 1 depicts the X-ray diffraction pattern of Form A of Example 1.

At least in part, this disclosure is directed to crystalline forms of hemioxalate salt of 6-O-(4-dimethylaminoethoxy) cinnamoyl fumagillol, and hydrates thereof. The disclosure also provides for pharmaceutical composition comprising a disclosed crystalline salt of 6-O-(4-dimethylaminoethoxy) cinnamoyl fumagillol, and a pharmaceutically acceptable carrier. The term "crystalline form" refers to a crystal form or modification that can be characterized by analytical methods such as, e.g., X-ray powder diffraction or Raman-spectroscopy. For example, provided herein is a drug substance comprising at least a detectable amount of a disclosed crystalline form of 6-O-(4-dimethylaminoethoxy)cinnamoyl fumagillol hemioxalate.

Provided herein is a crystalline form of 6-O-(4-dimethylaminoethoxy)cinnamoyl fumagillol, hemioxalate, characterized by a powder X-ray diffraction pattern having a characteristic peak in degrees 2θ at about 7.1 (referred to herein as "Form A"). In one embodiment, the crystalline form of 6-O-(4-dimethylaminoethoxy)cinnamoyl fumagillol, is characterized by a powder X-ray diffraction pattern that has a characteristic peak in degrees 2θ at about 2.3, or is characterized by a powder X-ray diffraction pattern that has a characteristic peak in degrees 2θ at about 4.7, or is characterized by a powder X-ray diffraction pattern that has a characteristic peak in degrees 2θ at about 7.1, or is characterized by a powder X-ray diffraction pattern that has a characteristic peak in degrees 2θ at about 9.5, or is characterized by a powder X-ray diffraction pattern that has a characteristic peak in degrees 2θ at about 11.9, or is characterized by a powder X-ray diffraction pattern that has a characteristic peak in degrees 2θ at about 12.9, or is characterized by a powder X-ray diffraction pattern that has a characteristic peak in degrees 2θ at about 13.4, or is characterized by a powder X-ray diffraction pattern that has a characteristic peak in degrees 2θ at about 14.3, or is characterized by a powder X-ray diffraction pattern that has a characteristic peak in degrees 2θ at about 14.6, or is characterized by a powder X-ray diffraction pattern that has a characteristic peak in degrees 2θ at about 15.6, or is characterized by a powder X-ray diffraction pattern that has a characteristic peak in degrees 2θ at about 16.8, or is characterized by a powder X-ray diffraction pattern that has a characteristic peak in degrees 2θ at about 20.3. In a further embodiment, the crystalline form is characterized by a powder X-ray diffraction pattern having at least one or more characteristic peaks in degrees 2θ at about 4.7, 7.1, and 13.4. In yet another embodiment, the crystalline form is characterized by a powder X-ray diffraction pattern having at least one or more characteristic peaks in degrees 2θ at 4.7, 7.1, 9.5, 12.9, 13.4, and 16.8. In some embodiments, the crystalline form is characterized by a powder X-ray diffraction pattern having at least one or more characteristic peaks in degrees 2θ at 2.3, 4.7, 7.1, 9.5, 11.9, 12.9, 13.4, 14.3, 14.6, 15.6, 16.8, and 20.3. The term "about" in this context means that there is an uncertainty in the measurements of the 2θ of ±0.5 (expressed in 2θ). For example, a contemplated crystalline form has a powder X-ray diffraction pattern shown in FIG. 1 or FIG. 2. In one embodiment, the powder X-ray diffraction pattern of the crystalline form was obtained using Cu Kα radiation. In a further example, a contemplated form has a $^1$H NMR spectrum substantially in accordance with the pattern shown in FIG. 7A or FIG. 7B.

Figure 3:
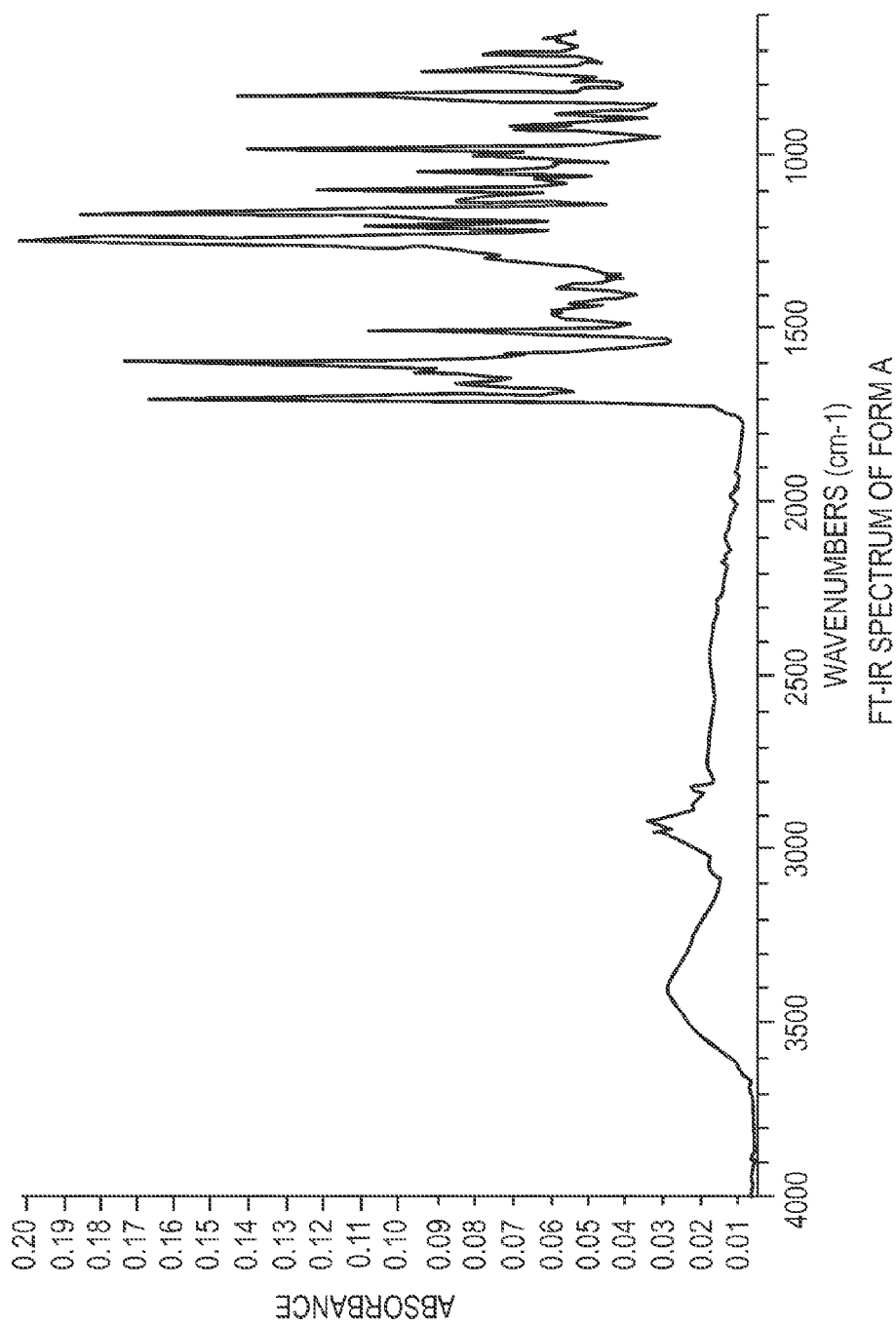
FIG. 3 depicts the FT-IR spectrum of the crystal form prepared by Example 2 (Form A).
Figure 4:
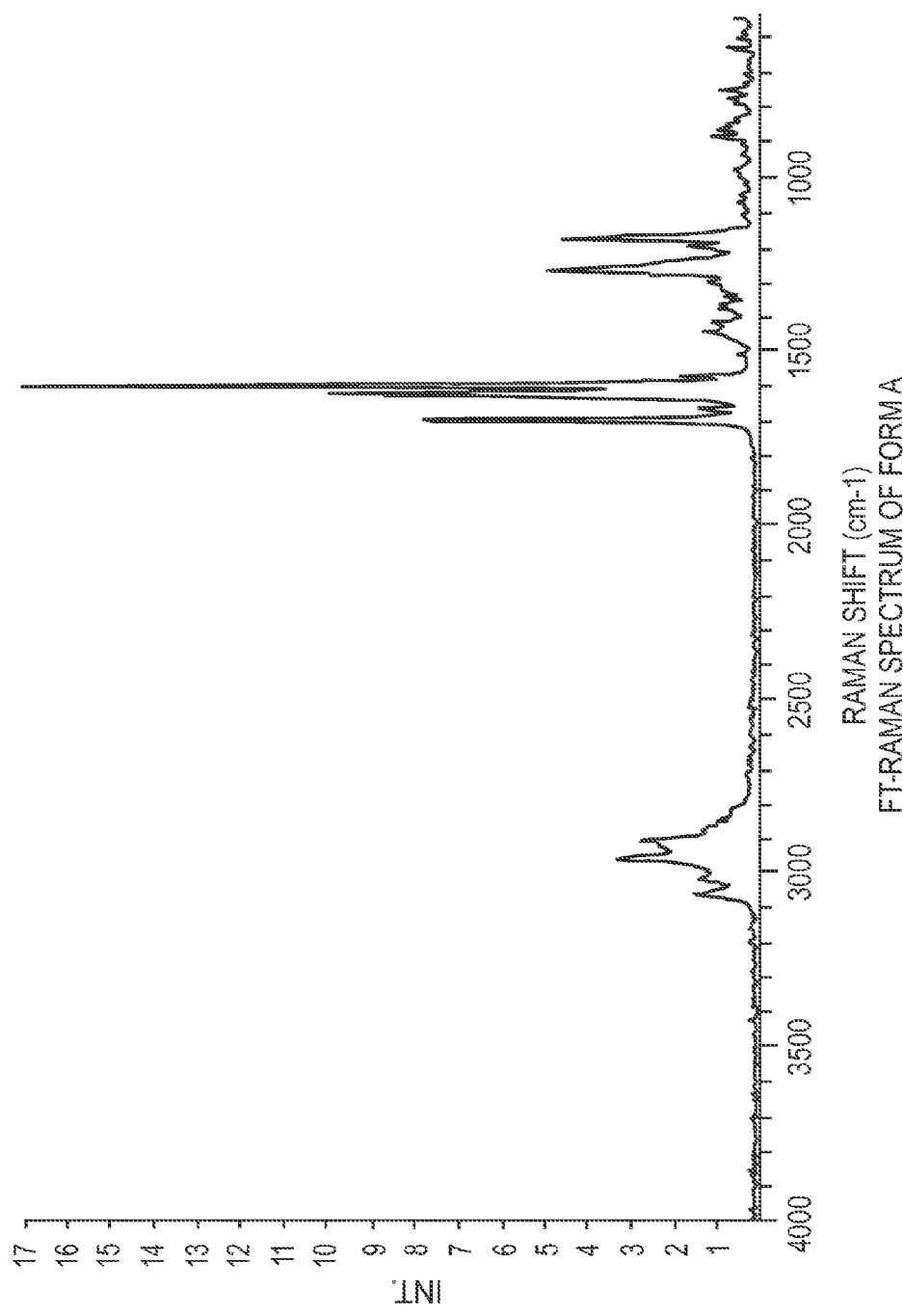
FIG. 4 depicts the FT-Raman spectrum of the crystal form prepared by Example 2 (Form A).
Figure 5:
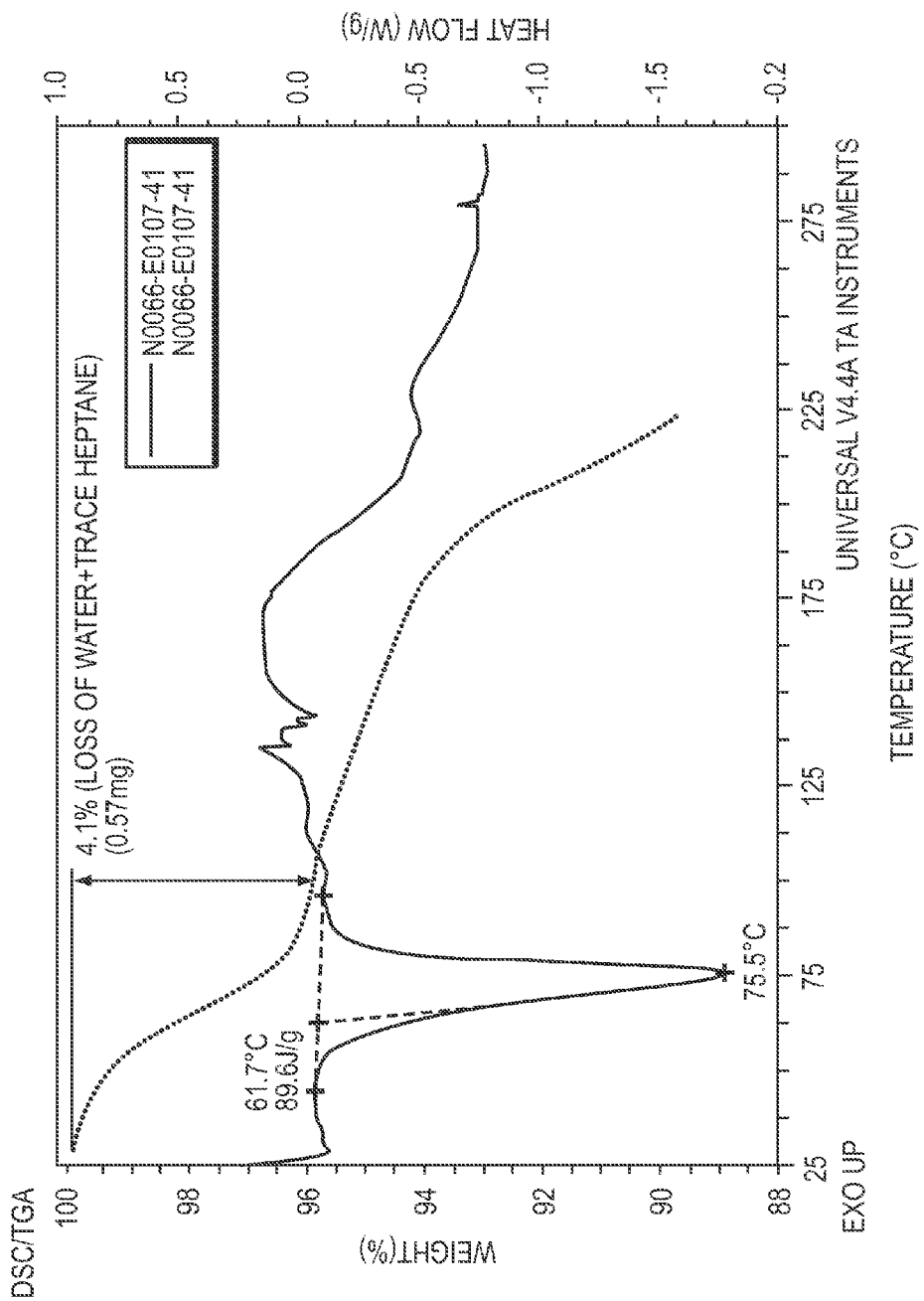
FIG. 5 depicts the characterization of Form A (Example 2) by differential scanning calorimetry (DSC) and thermogravimetric thermal analysis (TGA).
Figure 6:
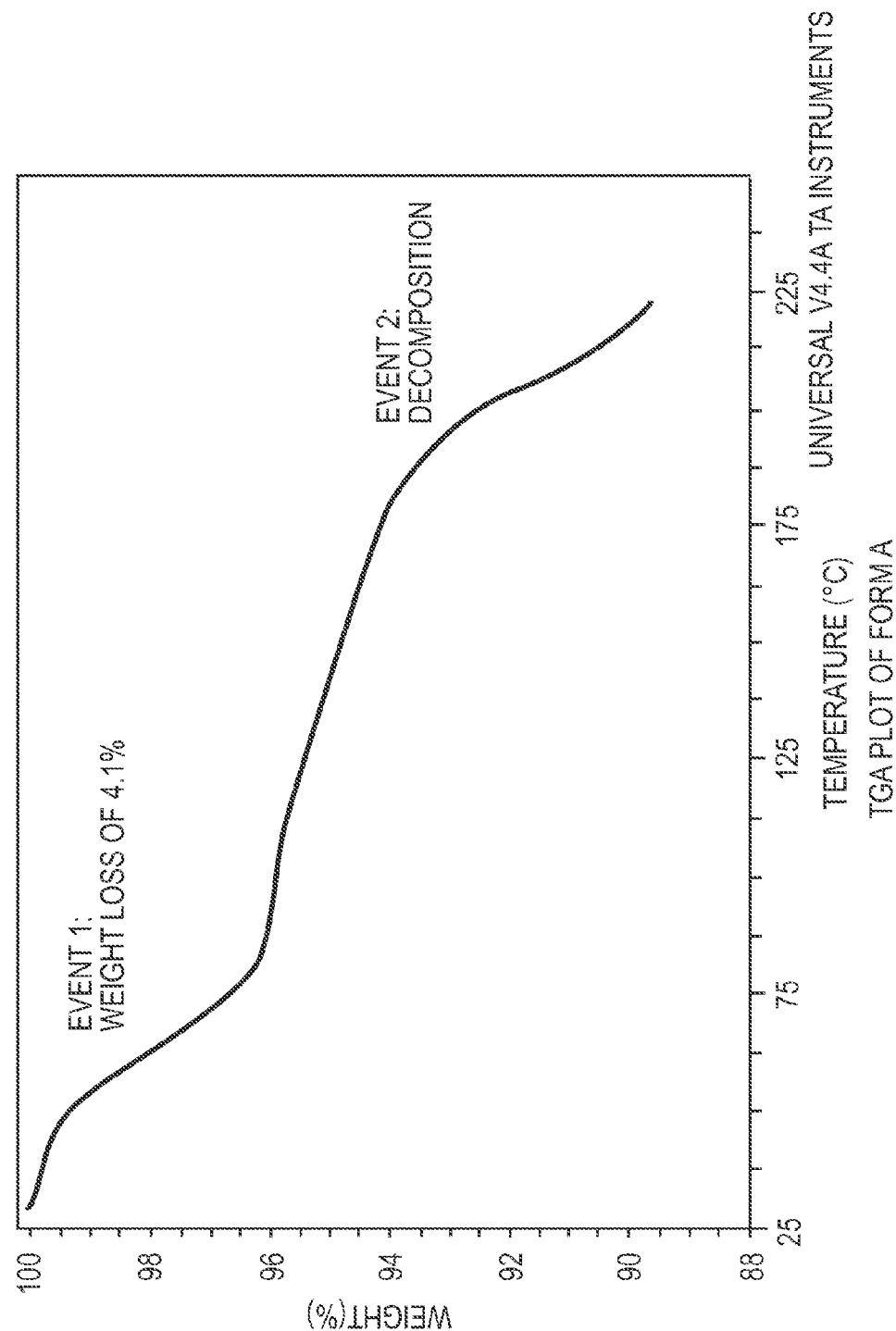
FIG. 6 depicts the characterization of Form A (Example 2) by thermogravimetric thermal analysis (TGA).

The crystalline form of Form A 6-O-(4-dimethylaminoethoxy)cinnamoyl fumagillol has an IR absorption spectrum having at least one or more characteristic peaks at about 1703, 1603, 1512, 1250, 1208, 1171, 1109, 1056, 986, 831 cm$^{-1}$. In this context, the term "about" means that the cm$^{-1}$ values can vary, e.g., up to ±5 cm$^{-1}$. A contemplated crystalline form is characterized by the IR absorption spectrum shown in FIG. 3. The crystalline form of Form A 6-O-(4-dimethylaminoethoxy)cinnamoyl fumagillol has a Raman spectrum having at least one or more characteristic peaks at about 3064, 2966, 2915, 1704, 1628, 1604, 1575, 1272, 1203, 1182, cm$^{-1}$. In this context, the term "about" means that the cm$^{-1}$ values can vary, e.g., up to ±5 cm$^{-1}$. A contemplated crystalline form is characterized by the Raman spectrum shown in FIG. 4. Contemplated crystalline forms disclosed herein may be substantially more stable as compared, for example, to amorphous free base and/or amorphous hemioxalate salt of 6-O-(4-dimethylaminoethoxy)cinnamoyl fumagillol. For example, a disclosed crystalline form (e.g., Form A), may be stored under practical and economical storage conditions, while retaining physical properties so that it may be manufactured into a dosage form. In an embodiment, a disclosed crystalline form may have improved chemical and/or physical stability when e.g., compounded in a pharmaceutical formulation, as compared to e.g., the amorphous form.

Hydrate forms of crystalline hemioxalate 6-O-(4-dimethylaminoethoxy)cinnamoyl fumagillol are contemplated, e.g., hemioxalate 6-O-(4-dimethylaminoethoxy)cinnamoyl fumagillol•(H$_2$O)$_m$, where m is a fractional or whole number between about 0 and about 4 inclusive. For example, contemplated herein are monohydrate or dihydrate forms of crystalline hemioxalate 6-O-(4-dimethylaminoethoxy)cinnamoyl fumagillol. In an embodiment, a disclosed crystalline hemioxalate compound may have a water level of about 3 to about 9 wt. percent %.

Also provided herein is a process for preparing a crystalline form of hemioxalate 6-O-(4-dimethylaminoethoxy)cinnamoyl fumagillol, e.g., Form A, comprising:

a) preparing a solution of a hemioxalate salt of 6-O-(4-dimethylaminoethoxy)cinnamoyl fumagillol in a solvent such as, e.g., ethyl acetate and/or heptane;

b) heating the solution to dissolve the 6-O-(4-dimethylaminoethoxy)cinnamoyl fumagillol;

c) adjusting the temperature so that solid precipitates out of the solution; and d) isolating the crystalline form of hemioxalate 6-O-(4-dimethylaminoethoxy)cinnamoyl fumagillol. In an exemplary embodiment, the solution comprises ethyl acetate and/or heptane. In another embodiment, the solution further comprises water. Other contemplated solvents include acetonitrile, cyclohexane, methanol, isopropanoyl, methyl isobutyl ketone, hexane, toluene, and/or tetrahydrofuran. In some embodiments, heating the solution comprises heating the solution to about 35° C. to about 55° C., e.g., to about 40° C.

In another embodiment, adjusting the temperature comprises cooling the solution to about 0° C. to about 10° C., e.g., to about 5° C. In one embodiment, adjusting temperature comprises cooling the solution to about 5° C. or less, or to about 2° C. to about 10° C.

Contemplated processes may also include incorporating or seeding a solution with an existing crystal of 6-O-(4-dimethylaminoethoxy)cinnamoyl fumagillol. For example, a process may include initially preparing a solution with amorphous or crystalline free base compound and oxalic acid, or may include initially preparing a solution with amorphous or crystalline hemioxalate 6-O-(4-dimethylaminoethoxy)cinnamoyl fumagillol.

In another embodiment, a different crystalline form of 6-O-(4-dimethylaminoethoxy)cinnamoyl fumagillol hemioxalate salt, characterized by a powder X-ray diffraction pattern having characteristic peaks in degrees 2θ at one or more of positions at about 2.2, 6.8, 9.1, 16.1, 18.4, 20.7, 23.1 (referred to herein as "Form B"), is provided. The term "about" in this context means that there is an uncertainty in the measurements of the 2θ of ±0.5 (expressed in 2θ). For example, a contemplated crystalline form has a powder X-ray diffraction pattern shown in FIG. 9.

Methods

In certain embodiments, the disclosure provides a method of treating and or ameliorating obesity in a patient in need thereof by administering an effective amount of a disclosed crystalline compound, e.g., hemioxalate 6-O-(4-dimethylaminoethoxy)cinnamoyl fumagillol (Form A). Also provided herein are methods for inducing weight loss in a patient in need thereof, comprising administering a disclosed crystalline compound.

Other contemplated methods of treatment include methods of treating or amelioriating an obesity-related condition or co-morbidity, by administering a crystalline compound disclosed herein to a subject. For example, contemplated herein are methods for treating type 2 diabetes in a patient in need thereof and/or method of treating a patient suffering from diabetes, for other contemplated diseases or disorders Exemplary co-morbidities or other disorders that may be treated by a disclosed compound may include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the disclosure provides a method of treating the above medical indications comprising administering to a subject in need thereof a therapeutically effective amount of a compound described herein. In certain other embodiments, a method of treating obesity in patient in need thereof is provided, comprising subcutaneously administering a composition comprising a disclosed crystalline form of 6-O-(4-dimethylaminoethoxy)cinnamoyl fumagillol, oxalate salt (Form A).

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines described above.

Administration

The crystalline compounds disclosed herein can be used as a medicament, e.g., in the form of pharmaceutical preparations for entereal, parenteral, or topical administration, and the contemplated methods disclosed herein may include administering enterally (e.g., orally), parenterally, or topically a disclosed crystalline compound.

Compositions

Another aspect of the disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, ocular, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for e.g., parenteral (subcutaneous or intravenous) applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Suspensions, in addition to the subject composition, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Suspensions suitable for intravenous administration may be formed, for example, with a particle size of compounds less than about 200 nm diameter.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Pharmaceutical compositions of this invention suitable for parenteral administration comprise a subject composition in combination with one or more pharmaceutically-acceptable sterile isotonic non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable non-aqueous carriers which may be employed in the pharmaceutical compositions of the invention include polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. For example, crystalline forms provided herein may be milled to obtain a particular particle size, and in at least some embodiments, such crystalline forms may remain substantially stable upon milling.

For example, provided herein is a composition suitable for subcutaneous administration, comprising a suspension of the disclosed crystalline form. Subcutaneous administration can be advantageous over intravenous administration, which typically requires a doctor visit, and can be more painful and invasive. A typical dose of the crystalline compound, when administered to a patient, may be about 1 mg to about 5 mg of compound.

EXAMPLES

The compounds described herein can be prepared in a number of ways based on the teachings contained herein and synthetic procedures known in the art.

X-ray powder diffraction (XRPD) data were obtained using a PANalytical X'Pert Pro diffractometer equipped with an X'Celerator detector. The sample was flattened on a zero-background silicon holder and was run immediately after preparation under ambient conditions. A continuous 2-theta scan range of 2° to 40° was used with a Cu Kα (1.5406 Å) radiation source and a generator power of 45 kV and 40 mA. A step size of 0.0167 degrees per 2-theta step was used and the sample was rotated at 30 rpm.

Raman spectra were recorded on a Nicolet NXR 9650 FT-Raman Spectrometer, at 4 cm$^{-1}$ resolution with excitation from a Nd:YVO4 laser (λ=1064 nm).

DSC thermograms were recorded on a TA Instruments Q1000 Differential Scanning calorimeter. The sample was weighed into an aluminium pan, a pan lid placed on top and lightly crimped without sealing the pan. The experiments were conducted using a heating rate of 15° C./min.

TGA thermograms were recorded on a TA Instruments Q5000 Themrogravimetric Analyzer. The sample was weighed into an aluminum pan, and experiments were conducted using a heating rate of 15° C./min.

1D 1H NMR spectra were acquired on a 500 MHz Varian Unity Inova NMR spectrometer. The sample was prepared in DMSO-d6 and referenced to TMS at 0.00 ppm.

Ion chromatography was performed on a Dionex ICS-3000 with a Dionex AS11HC 250×4 mm analytical column and a Dionex ASRS 300 suppressor. The analysis was done under isocratic condition using 20 mM NaOH mobile phase and a flow rate of 1 mL/min. Aqueous solutions of the sample and standard were injected at a fixed volume of 10 µL.

Example 1

Crystalline, Form A material of 6-O-(4-dimethylaminoethoxy)cinnamoyl fumagillol hemioxalate salt was prepared as follows:

Approximately 18 mg (0.037 mmol) of 6-O-(4-dimethylaminoethoxy)cinnamoyl fumagillol (free base) was combined with acetonitrile/heptane mixture (1:4, 400 µL) and oxalic acid (3M in THF, 6.1 µL, 0.5 eq). The solvent was evaporated to afford crystalline Form A.

Figure 2:
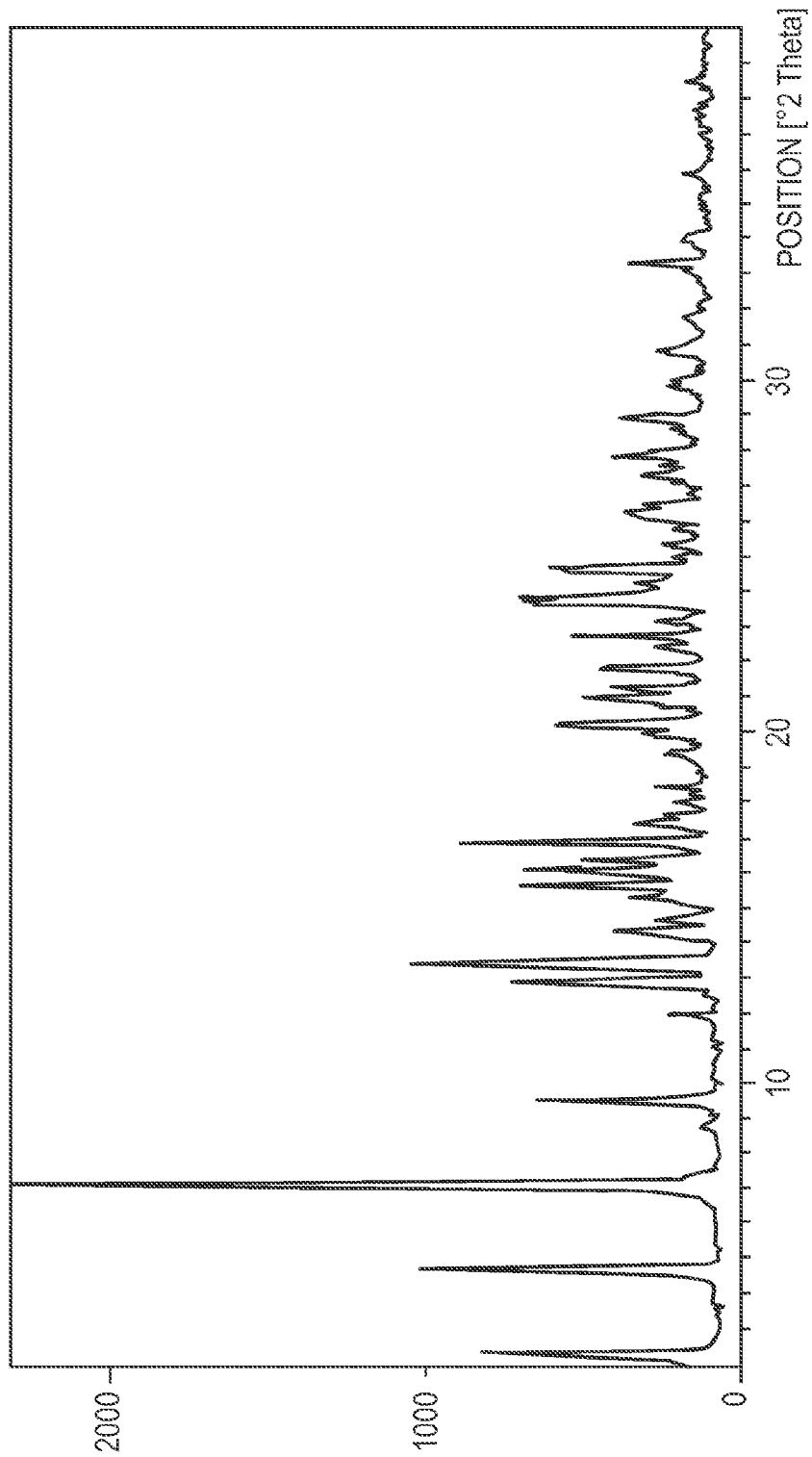
FIG. 2 depicts the X-ray diffraction pattern of Form A of Example 2.

XRPD analysis was conducted on the solid crystals (Form A). The XRPD is shown in FIG. 1.

Example 2

Crystalline, Form A material of 6-O-(4-dimethylaminoethoxy)cinnamoyl fumagillol hemioxalate was scaled up as follows:

6-O-(4-dimethylaminoethoxy)cinnamoyl fumagillol (free base) (1.2 g, 2.4 mmol) was combined with ethyl acetate (5 mL), heptane (10 mL) and water (200 uL) in a 30-mL reaction vessel. A 3M solution of oxalic acid in THF (405 uL, 1 equiv) was added in a dropwise fashion, which resulted in immediate precipitation. The mixture was seeded with Form A crystals and the suspension stirred at room temperature for 5 minutes, was heated to 40° C. for 30 minutes, and was cooled to 5° C. at a rate of 2° C./minute. After stirring for ca. 2 h at 5° C., the slurry was filtered under nitrogen in a jacketed Buchner funnel, which was maintained at 5° C. The solid was washed with heptane (2 mL) and air-dried at room temperature for two days to afford Form A (1.15 g, 81% yield). The Form A material was characterized by XPRD, FT-Raman and FT-IR and was shown to be consistent with other Form A material. The product, after correcting for weight loss at about 100° C., contains 7.9% w/w oxalate by ion chromatography, consistent with hemioxalate stoichiometry.

The XRPD pattern, FT-IR spectrum, FT-Raman spectrum, DSC trace, and TGA plot of the crystalline material (Form A) are depicted in FIG. 2, FIG. 3, FIG. 4, FIG. 5, and FIG. 6, respectively.

The characteristic XRPD peaks for Form A (FIG. 2) are seen below in Table 1, and the characteristic FT-IR absorption bands (FIG. 3) and FT-Raman bands (FIG. 4) for Form A are seen below in Tables 2 and 3, respectively.

TABLE 1

| Position [°2 Th.] | d-spacing [Å] |
| --- | --- |
| 2.3 | 37.7 |
| 4.7 | 18.7 |

TABLE 1-continued

| Position [°2 Th.] | d-spacing [Å] |
| --- | --- |
| 7.1 | 12.4 |
| 9.5 | 9.3 |
| 11.9 | 7.4 |
| 12.9 | 6.9 |
| 13.4 | 6.6 |
| 14.3 | 6.2 |
| 14.6 | 6.0 |
| 15.6 | 5.7 |
| 16.8 | 5.3 |
| 20.3 | 4.4 |

TABLE 2

| FT-IR Absorption Bands, $cm^{-1}$ |
| --- |
| 831 |
| 986 |
| 1056 |
| 1109 |
| 1171 |
| 1208 |
| 1250 |
| 1512 |
| 1603 |
| 1703 |

TABLE 3

| FT-Raman Bands, $cm^{-1}$ |
| --- |
| 1182 |
| 1203 |
| 1272 |
| 1575 |
| 1604 |
| 1628 |
| 1704 |
| 2915 |
| 2966 |
| 3064 |

Figure 7A:
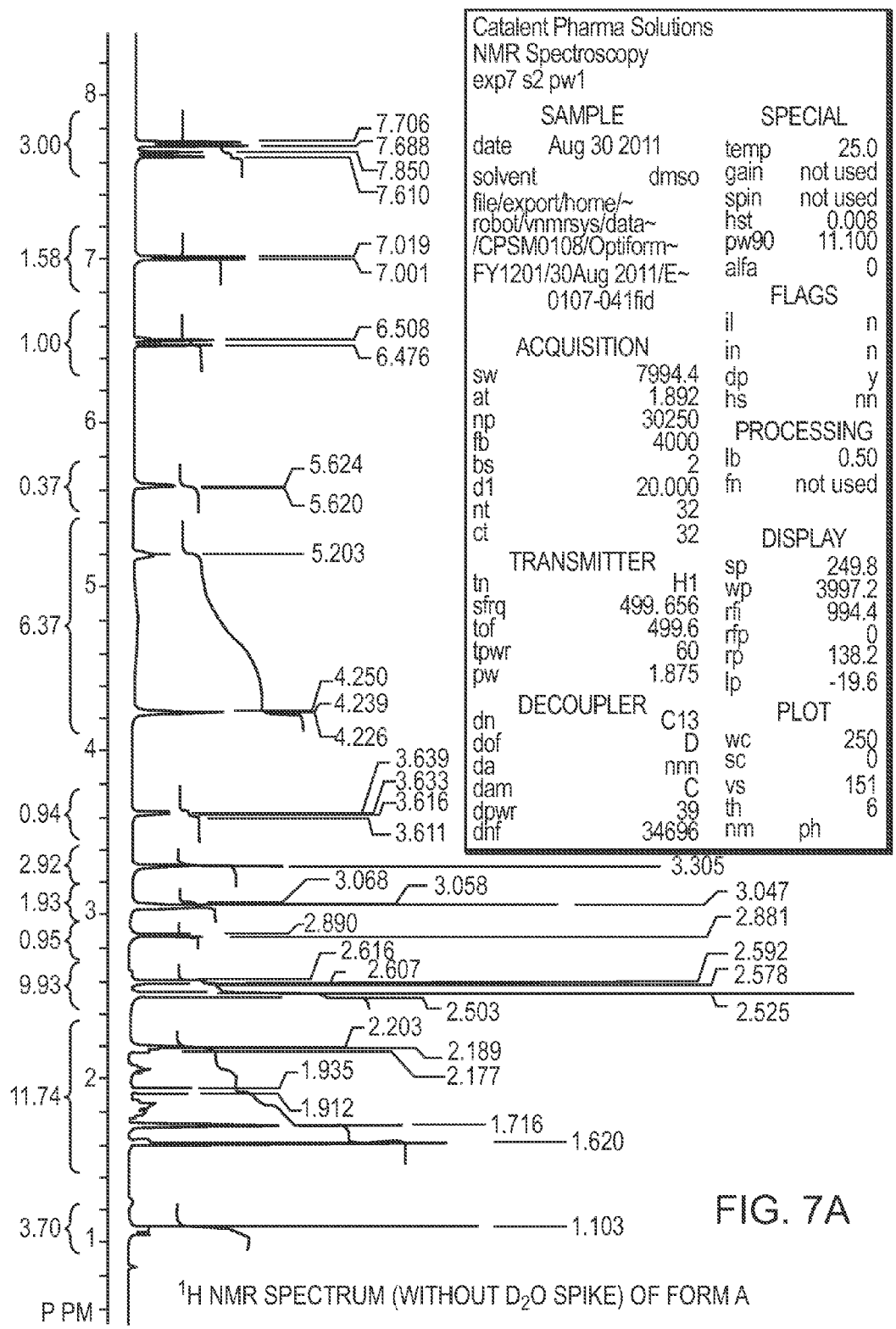
FIGS. 7A and B depict the NMR spectra of the dissolved crystal form prepared by Example 2.
Figure 7B:
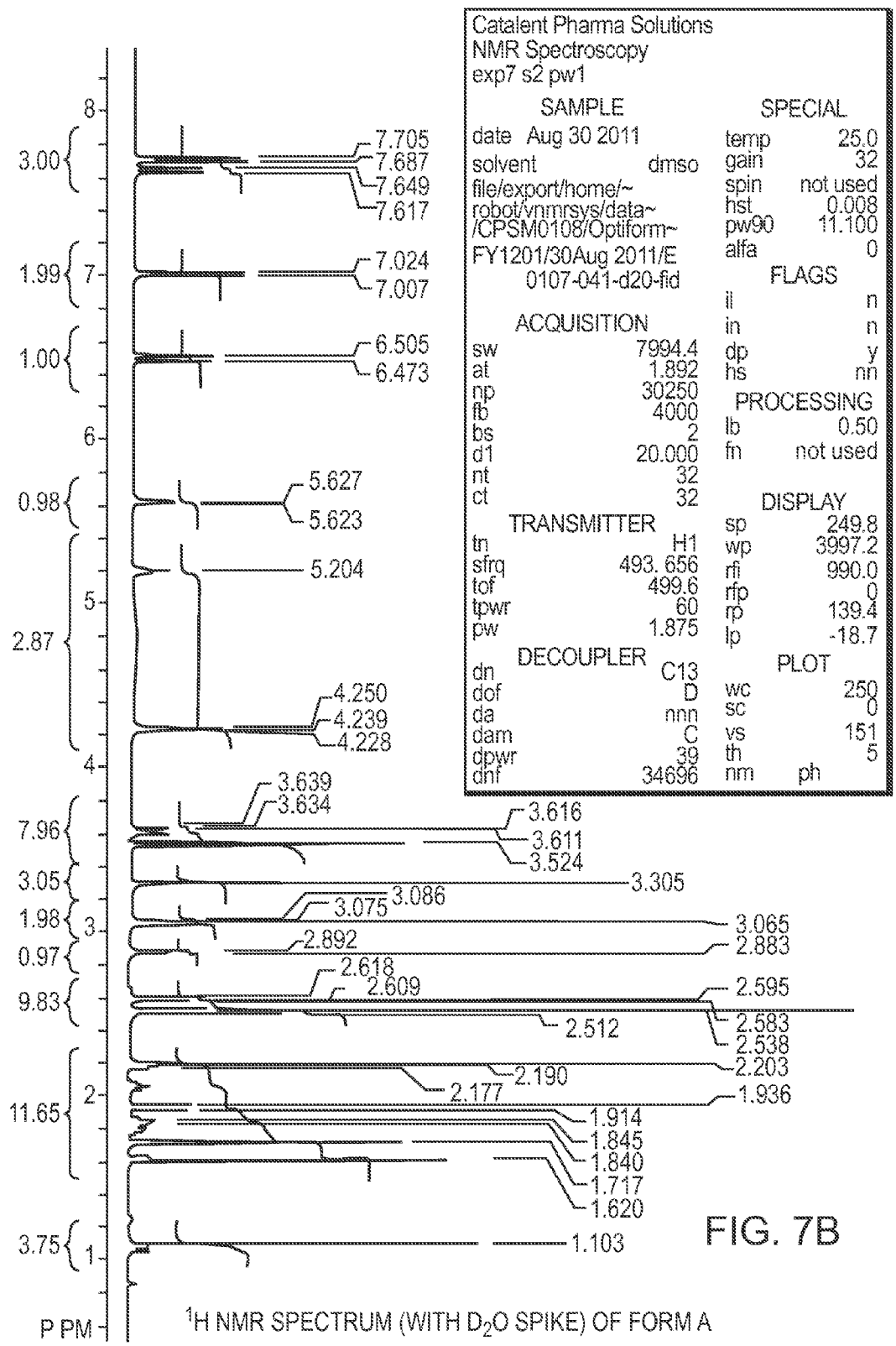

The $^1$H NMR spectrum of the crystalline material (Form A) are depicted in FIG. 7A (without D$_2$O spike) and FIG. 7B (with D$_2$O spike). The characteristic $^1$H NMR peaks of a sample of the crystalline material (Form A) are as follows:

FIG. 7A: (δ, ppm) 7.706, 7.688, 7.650, 7.618, 7.019, 7.001, 6.508, 6.476, 5.624, 5.620, 5.203, 4.250, 4.239, 4.228, 3.639, 3.633, 3.616, 3.611, 3.305, 3.068, 3.058, 3.047, 2.890, 2.881, 2.616, 2.607, 2.592, 2.579, 2.525, 2.503, 2.203, 2.189, 2.177, 1.935, 1.912, 1.716, 1.620, 1.103.

FIG. 7B: (δ, ppm) 7.705, 7.687, 7.649, 7.617, 7.024, 7.007, 6.505, 6.473, 5.627, 5.623, 5.204, 4.250, 4.239, 4.228, 3.639, 3.634, 3.616, 3.611, 3.524, 3.305, 3.086, 3.075, 3.065, 2.892, 2.883, 2.618, 2.609, 2.595, 2.583, 2.538, 2.512, 2.203, 2.190, 2.177, 1.936, 1.914, 1.845, 1.840, 1.717, 1.620, 1.104.

Example 3

Crystalline, Form A material of 6-O-(4-dimethylaminoethoxy)cinnamoyl fumagillol hemioxalate was prepared as follows:

Approximately 168 mg (0.337 mmol) of 6-O-(4-dimethylaminoethoxy)cinnamoyl fumagillol (free base) was combined with acetonitrile/heptane mixture (1:4, 1.5 mL) and oxalic acid (3M in THF, 56.1 µL, 0.5 eq) (note: the solvent mixture was biphasic). Seeds of Form A were observed to dissolve in the mixture. The resulting mixture was cycled several times by repeated evaporation to dryness and re-suspension in several solvents and solvent mixtures in an attempt to produce free-flowing crystalline material. After evaporation to dryness at 40° C., the sample was dissolved in ethyl acetate (500 µL) and precipitated by heptane (1 mL). The turbid mixture was stirred at room temperature for ca. 2 hours. To the resulting slurry, ethyl acetate (50 µL) was added and the sample was stirred overnight at room temperature. The following day, the sample was heated to 40° C. for 2 hours then cooled to 5° C. at 0.1° C./min. A white crystalline material (71 mg) was produced. FT-Raman and XRPD data of the product were consistent with Form A.

Example 4

Crystalline, Form A material of 6-O-(4-dimethylaminoethoxy)cinnamoyl fumagillol hemioxalate was prepared as follows:

Approximately 123 mg (0.245 mmol) of 6-0-(4-dimethylaminoethoxy)cinnamoyl fumagillol (free base) was combined with ethyl acetate (500 µL). A 3M solution of oxalic acid in THF (40.9 µL, 0.5 eq) was added in a dropwise fashion, which resulted in immediate precipitation. After the addition of seed crystals of Form A (from Example 3), ethyl acetate was added and the resulting slurry was stirred overnight, thermocycling between 40 to 5° C. A white amorphous precipitate was observed, but an addition of water (20 µL) produced a solution. Heptane was slowly added until the mixture was turbid (total heptane volume was 1.3 mL). Additional crystal seeds of Form A were added and the slurry was cooled down over 17 h with stirring to 5° C. A free-flowing slurry of crystalline material was obtained. Prior to isolation and while held at room temperature, the precipitate was observed to turn gummy. The gummy precipitate reverted back to free-flowing slurry upon cooling to 5° C. The sample was filtered quickly and allowed to air-dry. The XRPD pattern of the product was consistent with Form A.

Example 5

Figure 8A:
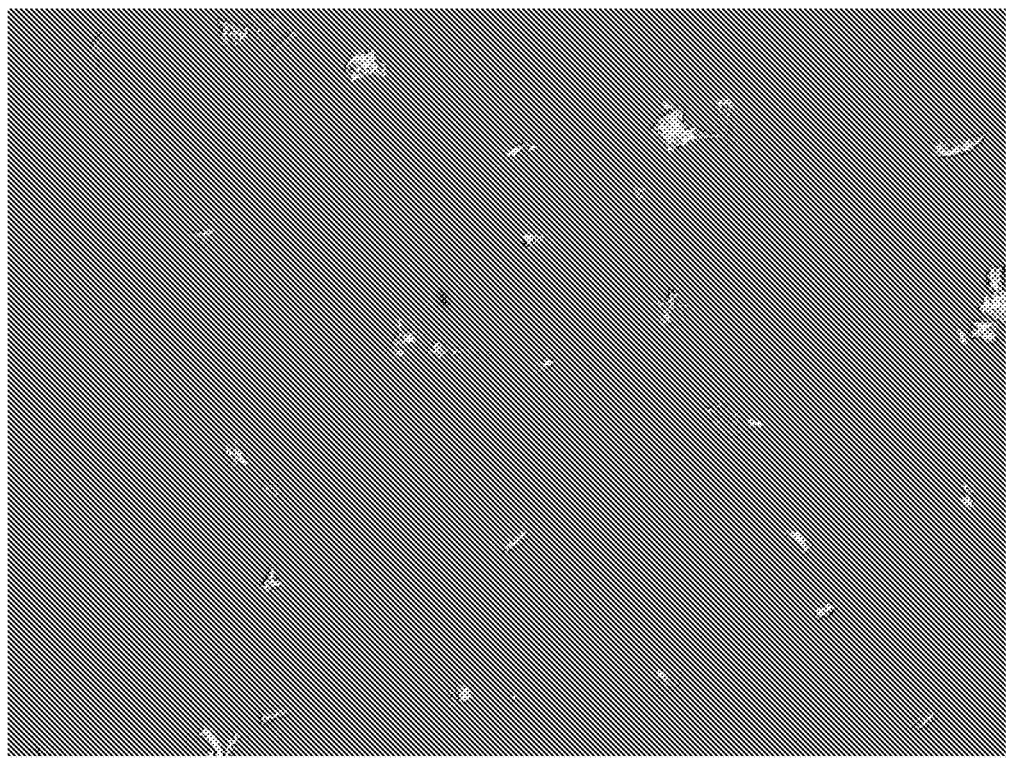
FIG. 8 (A) is a micrograph of amorphous hemioxalate material, which was utilized as starting material for Example 5, and (B) is the X-ray diffraction pattern of amorphous material used as starting material for Example 5.
Figure 8B:
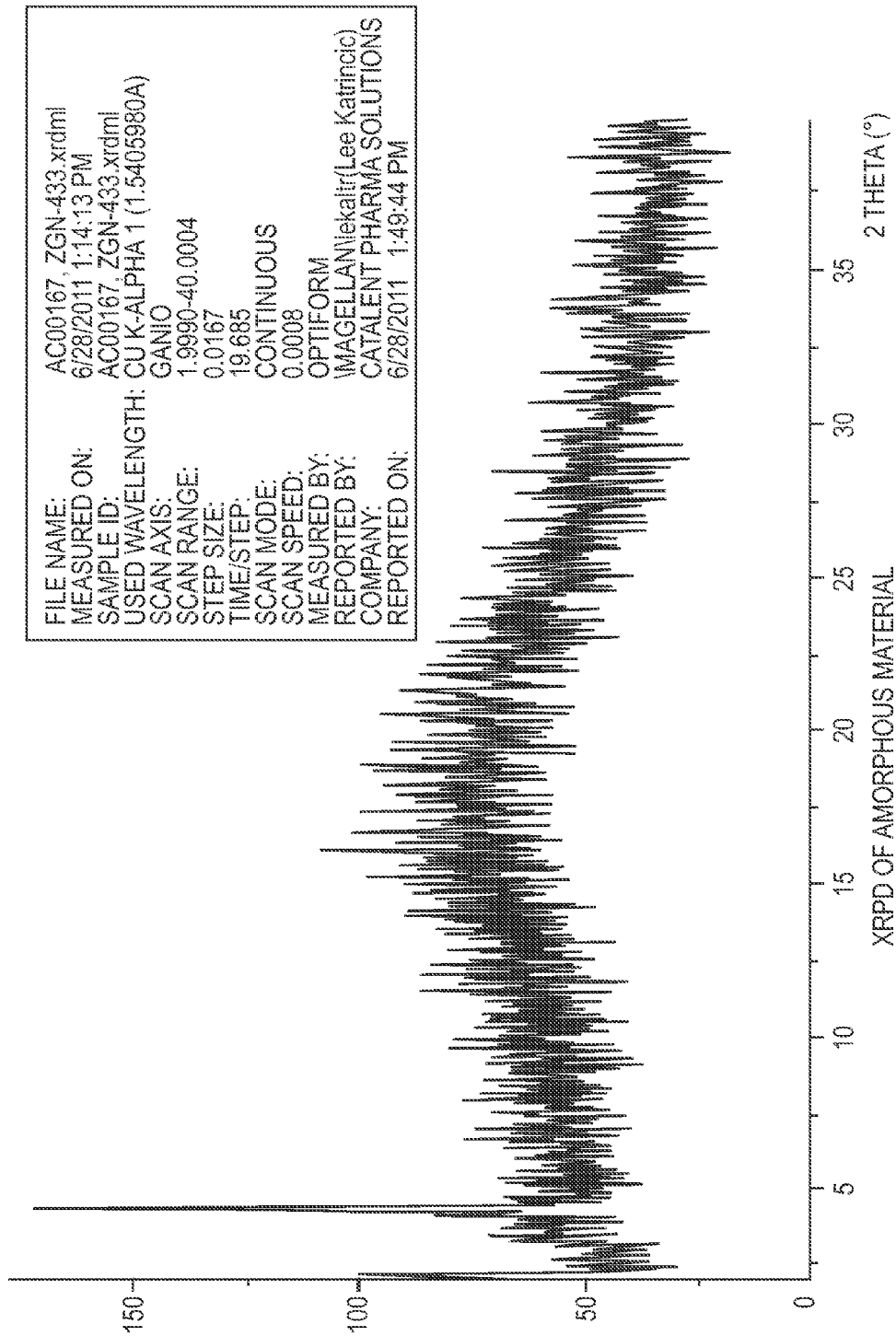

Crystalline, Form B material of 6-O-(4-dimethylaminoethoxy)cinnamoyl fumagillol hemioxalate was prepared as follows:

Approximately 10 mg of amorphous 6-O-(4-dimethylaminoethoxy)cinnamoyl fumagillol hemioxalate salt compound (see FIGS. 8A and 8B for characterization of amorphous material) was weighed into a 2-mL vial and suspended in toluene (100 uL). The suspension was heated to 50° C. and allowed to stir for 17 h. The isothermal slurry afforded crystalline Form B as a glassy solid that when isolated underwent a change in appearance from translucent to a white semitacky powder.

Figure 9:
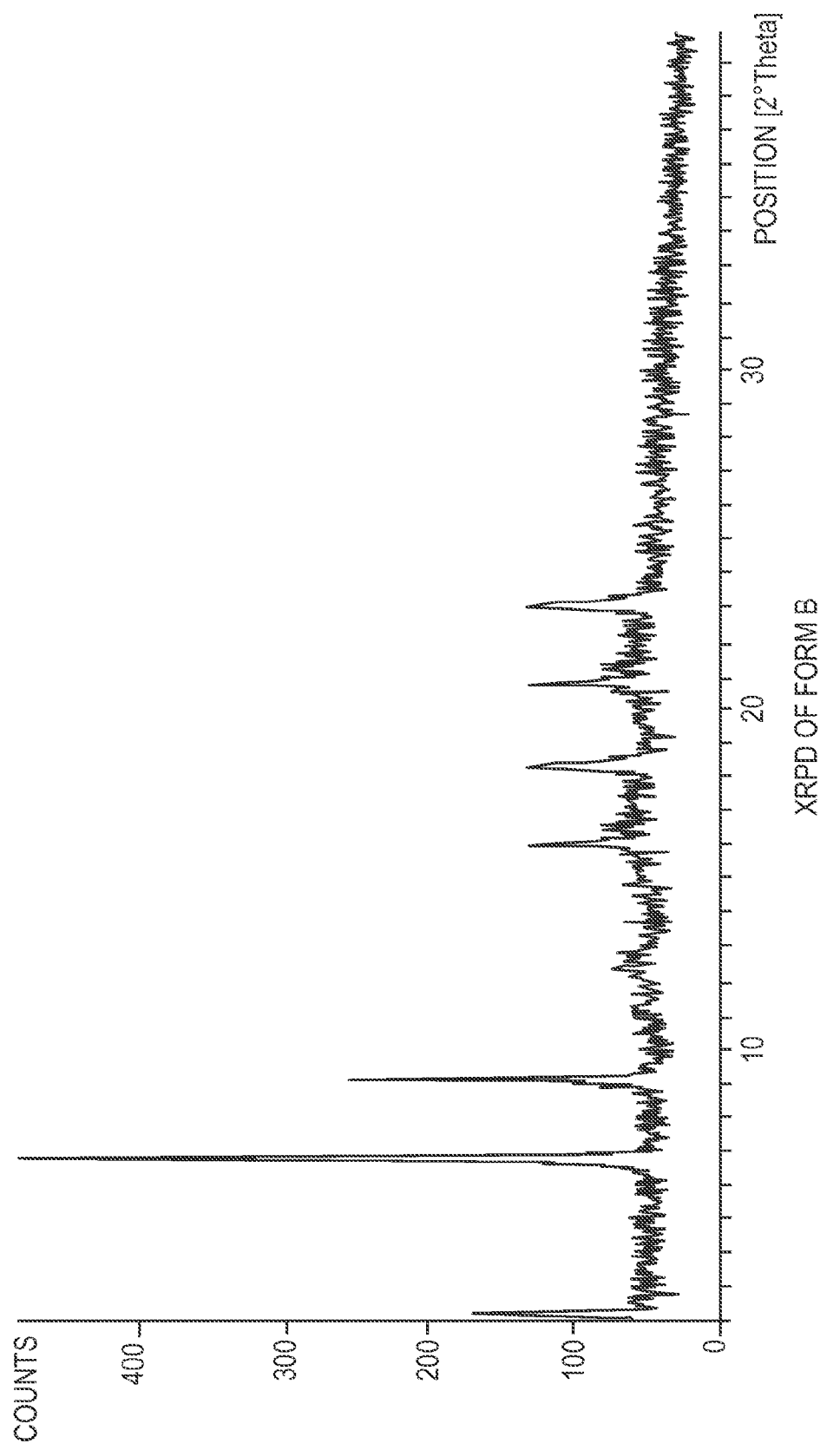
FIG. 9 is the X-ray diffraction pattern of Form B of Example 5.

XRPD analysis was conducted on the solid crystals (Form B), and the diffraction peaks indicate some crystallinity. The XRPD is shown in FIG. 9 and the characteristic XRPD peaks are seen below in Table 4.

TABLE 4

| Position [°2 Th.] | d-spacing [Å] |
|---|---|
| 2.2 | 39.7 |
| 6.8 | 13.0 |

TABLE 4-continued

| Position [°2 Th.] | d-spacing [Å] |
|---|---|
| 9.1 | 9.7 |
| 16.1 | 5.5 |
| 18.4 | 4.8 |
| 20.7 | 4.3 |
| 23.1 | 3.9 |

Form B was observed to be metastable relative to Form A.

Example 6

Crystalline, Form A material of 6-O-(4-dimethylaminoethoxy)cinnamoyl fumagillol hemioxalate was prepared as follows:

Approximately 15 mg of amorphous 6-O-(4-dimethylaminoethoxy)cinnamoyl fumagillol hemioxalate salt compound (see FIGS. 8A and 8B for characterization of amorphous material) was weighed into a 2-mL vial and suspended in heptane (500 uL). The resulting slurry was stirred at room temperature for 15 minutes and seed crystals of Form B were added. The slurry was stirred for four days at room temperature. After filtration, Form A was provided as a free-flowing white powder (different XRPD pattern than Form B seed crystals).

Figure 10:
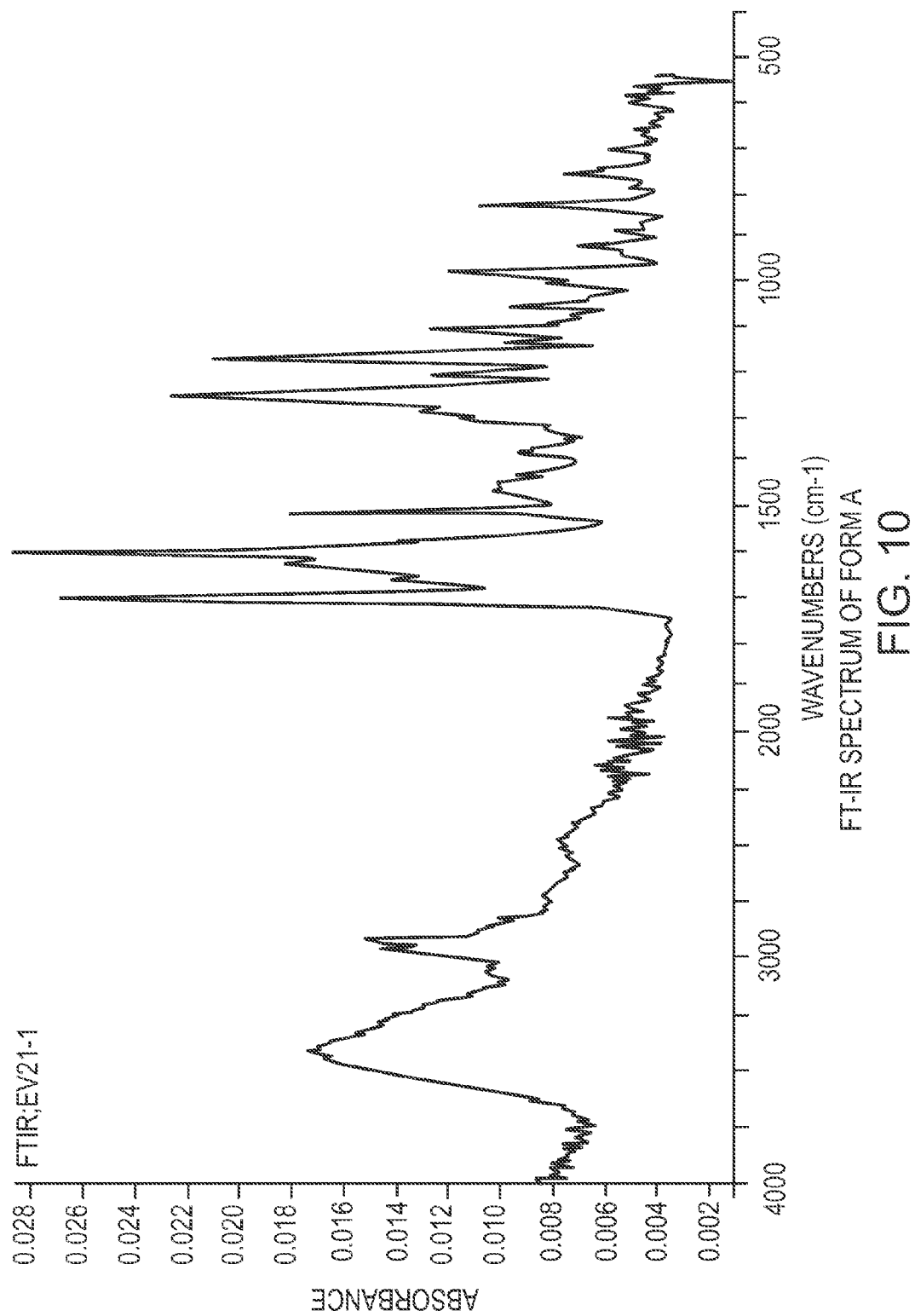
FIG. 10 depicts the FT-IR spectrum of the crystal form prepared by Example 6 (Form A).
Figure 11:
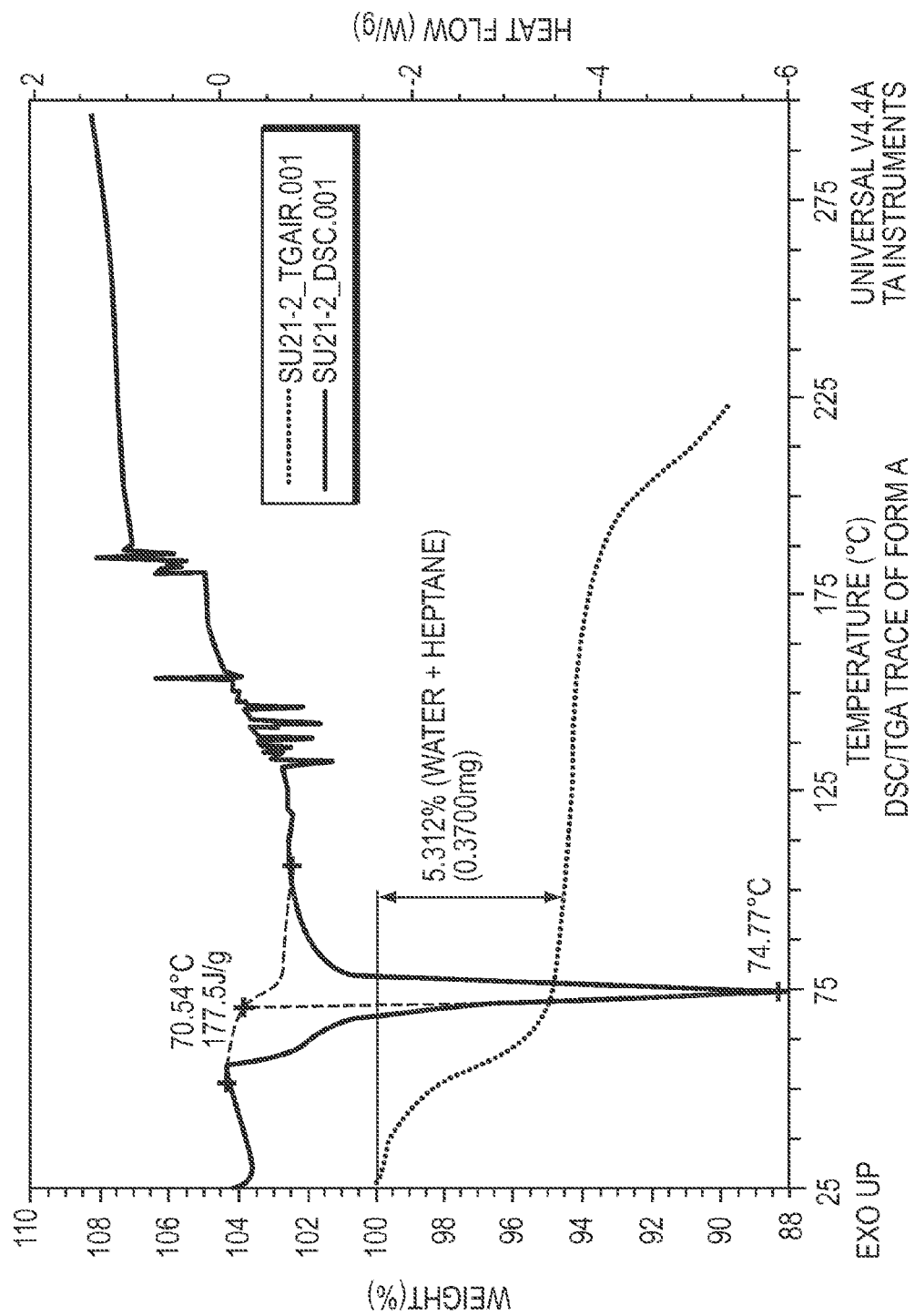
FIG. 11 depicts the characterization of Form A (Example 6) by differential scanning calorimetry (DSC) and thermogravimetric/differential thermal analysis (TGA).
Figure 12:
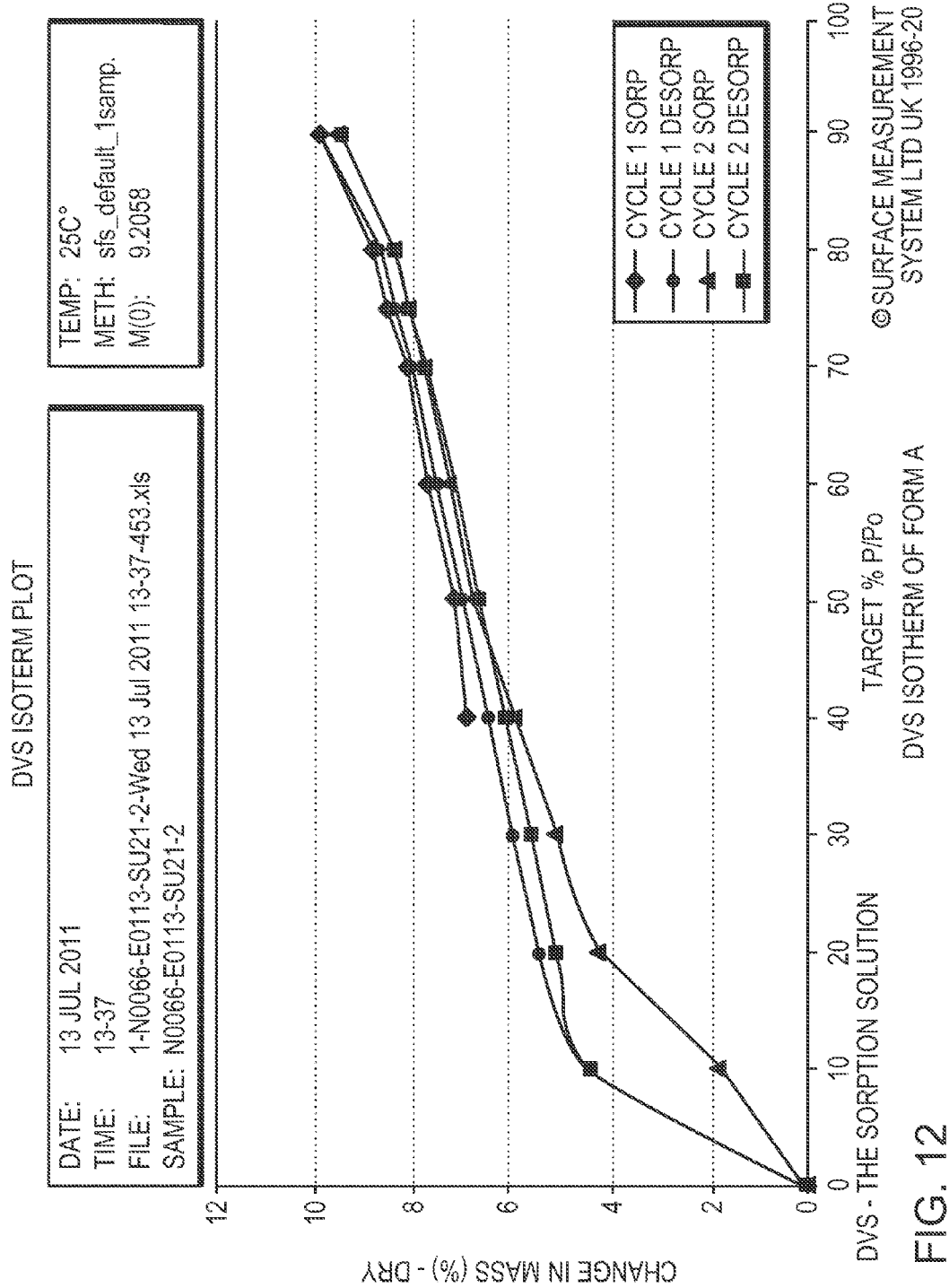
FIG. 12 depicts the characterization of Form A (Example 6) by dynamic vapor sorption (DVS).

FIG. 10 depicts the FT-IR spectrum of the crystalline material (Form A). FIG. 11 depicts the DSC/TGA trace of the crystalline material (Form A). The DVS isotherm plot of the crystalline material (Form A) is depicted in FIG. 12.

Example 7

Crystalline, Form A material of 6-O-(4-dimethylaminoethoxy)cinnamoyl fumagillol hemi oxalate was scaled up as follows:

Approximately 76 mg of amorphous 6-O-(4-dimethylaminoethoxy)cinnamoyl fumagillol hemioxalate salt compound (see FIGS. 8A and 8B for characterization of amorphous material) was suspended in heptane (2 mL) in a 4-mL vial. The resulting slurry was stirred for 10 minutes at room temperature and seeded with Form A crystals (ca. 1 mg). The slurry stirred for 3 days at room temperature. After filtration, the crystalline white powder (52 mg, 68% yield) was afforded. The XPRD pattern matched that seen in FIG. 2.

The FT-Raman spectrum of the crystalline material (Form A) is depicted in FIG. 13.

Example 8

A challenge stability study was carried out with amorphous and crystalline forms. Samples were stored in sealed vials and stored at room temperature (25° C.) and 40° C. Samples were assayed at various times with a stability-indicating HPLC assay. Retained potency was determined and physical description was observed. Results are shown in Table 5:

TABLE 5

| Sample | Time zero | | 25° C. −8 days | | 25° C. −12 days | | 40° C. −5 days | |
|---|---|---|---|---|---|---|---|---|
| | Physical description | % Purity (by peak area) | Physical Description | % Purity (by peak area) | Physical Description | % Purity (by peak area) | Physical Description | % Purity (by peak area) |
| Amorphous | Free flowing white powder | 94.98 | White powder stuck to glass vials | 86.58 | White powder stuck to glass vials | 83.88 | White powder stuck to glass vials | 86.91 |
| Crystalline | Free flowing white powder | 97.91 | Free flowing white powder | 97.86 | Free flowing white powder | 97.84 | Free flowing white powder | 97.72 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

I claim:

1. A crystalline form of a hemioxalate salt of 6-O-(4-dimethylaminoethoxy)cinnamoyl fumagillol, characterized by a powder X-ray diffraction pattern having a characteristic peak in degrees 2θ at about 7.1.

2. The crystalline form of claim 1, characterized by a powder X-ray diffraction pattern having characteristic peaks in degrees 2θ at about 4.7, 7.1, and 13.4.

3. The crystalline form of claim 2, characterized by a powder X-ray diffraction pattern having characteristic peaks in degrees 2θ at about 4.7, 7.1, 9.5, 12.9, 13.4, and 16.8.

4. The crystalline form of claim 3, characterized by a powder X-ray diffraction pattern having characteristic peaks in degrees 2θ at 2.3, 4.7, 7.1, 9.5, 11.9, 12.9, 13.4, 14.3, 14.6, 15.6, 16.8, and 20.3.

5. The crystalline form of claim 1, comprising the powder X-ray diffraction pattern shown in FIG. 2.

6. The crystalline form of claim 1, wherein the powder X-ray diffraction pattern was obtained using Cu Kα radiation.

7. A crystalline form of 6-O-(4-dimethylaminoethoxy)cinnamoyl fumagillol hemioxalate, characterized by a powder X-ray diffraction pattern having peaks in degrees 2θ at one or more of positions at about 2.2, 6.8, 9.1, 16.1, 18.4, 20.7, 23.1.

8. A process for preparing the crystalline form of claim 1, comprising:
 a) preparing a solution of a hemioxalate salt of 6-O-(4-dimethylaminoethoxy)cinnamoyl fumagillol in a solvent comprising ethyl acetate and heptane;
 b) heating the solution to dissolve the hemioxalate salt of 6-O-(4-dimethylaminoethoxy)cinnamoyl fumagillol;
 c) adjusting the temperature so that solid precipitates out of the solution; and
 d) isolating the crystalline form of the hemioxalate salt of 6-O-(4-dimethylaminoethoxy)cinnamoyl fumagillol.

9. The process of claim 8, wherein heating the solution comprises heating the solution to about 35° C. to about 55° C.

10. The process of claim 8, wherein heating the solution comprises heating the solution to about 40° C.

11. The process of claim 8, wherein adjusting temperature comprises cooling the solution to about 5° C. or less, or to about 2° C. to about 10° C.

* * * * *